US011775588B1

(12) United States Patent
Lawyer et al.

(10) Patent No.: US 11,775,588 B1
(45) Date of Patent: Oct. 3, 2023

(54) METHODS FOR PROVIDING USERS WITH ACCESS TO DATA USING ADAPTABLE TAXONOMIES AND GUIDED FLOWS

(71) Applicant: Cigna Intellectual Property, Inc., Wilmington, DE (US)

(72) Inventors: Matthew T. Lawyer, Santa Monica, CA (US); Benjamin Grimes, Los Angeles, CA (US); Andrew J. Young, Los Angeles, CA (US)

(73) Assignee: Cigna Intellectual Property, Inc., Wilmington, DE (US)

( * ) Notice: Subject to any disclaimer, the term of this patent is extended or adjusted under 35 U.S.C. 154(b) by 77 days.

(21) Appl. No.: 16/726,347

(22) Filed: Dec. 24, 2019

(51) Int. Cl.
*G06F 7/00* (2006.01)
*G06F 16/906* (2019.01)
*G06F 16/9032* (2019.01)
*G06F 16/13* (2019.01)
*G06F 16/14* (2019.01)
*G06F 16/909* (2019.01)

(52) U.S. Cl.
CPC .......... *G06F 16/906* (2019.01); *G06F 16/134* (2019.01); *G06F 16/144* (2019.01); *G06F 16/909* (2019.01); *G06F 16/9032* (2019.01)

(58) Field of Classification Search
CPC .... G06F 16/906; G06F 16/134; G06F 16/144; G06F 16/909; G06F 16/9032; G06F 16/35; G06F 16/45; G06F 16/185; G06F 16/3323
See application file for complete search history.

(56) References Cited

U.S. PATENT DOCUMENTS

| | | | | |
|---|---|---|---|---|
| 5,553,226 A * | 9/1996 | Kiuchi | ................... | G06T 11/206 715/853 |
| 6,868,525 B1 * | 3/2005 | Szabo | .................... | G06Q 30/02 715/738 |
| 6,990,485 B2 * | 1/2006 | Forman | ................ | G06K 9/6282 707/737 |
| 7,050,990 B1 * | 5/2006 | Chu | .................... | G06Q 30/0251 705/14.71 |
| 7,672,951 B1 * | 3/2010 | Bierner | ................... | G06F 16/93 707/999.01 |
| 7,802,183 B1 * | 9/2010 | Essin | ................... | G06Q 10/087 715/255 |

(Continued)

*Primary Examiner* — Mohammed R Uddin
(74) *Attorney, Agent, or Firm* — Stinson LLP

(57) ABSTRACT

A classification computing system provides adaptable taxonomies to facilitate user navigation of complex information systems. The classification computer includes a memory and a processor. The processor is configured to receive a collection of file indices from the information server. The processor is configured to apply a taxonomical classification algorithm to the collection to generate a collection of classified file indices. The classified file is associated with at least one taxonomical classification. The processor is further configured to apply a flow algorithm to the collection to generate at least one flow path used to provide a user access to a first subset of taxonomical classifications and restricts access to at least a second subset of taxonomical classifications. The flow path is responsive to user input parameters. The processor is configured to receive a user input parameter. The processor is additionally configured to provide the flow path to the user computing device.

20 Claims, 11 Drawing Sheets

(56) References Cited

U.S. PATENT DOCUMENTS

| | | | |
|---|---|---|---|
| 8,185,552 B1* | 5/2012 | Chow | G06Q 30/02 |
| | | | 707/791 |
| 8,423,565 B2 | 4/2013 | Redlich | |
| 8,463,817 B2 | 6/2013 | Chow | |
| 9,990,495 B2 | 6/2018 | Parinov | |
| 10,360,380 B2 | 7/2019 | Maisel | |
| 10,445,116 B1 | 10/2019 | Lauka | |
| 10,992,547 B2* | 4/2021 | Varney | H04L 67/26 |
| 2001/0044837 A1* | 11/2001 | Talib | G06Q 30/0601 |
| | | | 709/219 |
| 2002/0059003 A1* | 5/2002 | Ruth | G06F 16/972 |
| | | | 700/19 |
| 2004/0111438 A1* | 6/2004 | Chitrapura | G06F 16/00 |
| 2005/0144162 A1* | 6/2005 | Liang | G06F 16/152 |
| 2005/0171746 A1* | 8/2005 | Thalhammer-Reyero | |
| | | | G16B 5/00 |
| | | | 703/2 |
| 2005/0289168 A1* | 12/2005 | Green | G06F 16/3322 |
| 2005/0289199 A1* | 12/2005 | Aphinyanaphongs | G06F 16/35 |
| 2006/0009912 A1 | 1/2006 | Henricus | |
| 2006/0200455 A1* | 9/2006 | Wilson | G06F 16/9535 |
| 2006/0282465 A1 | 12/2006 | Sharma | |
| 2007/0156677 A1* | 7/2007 | Szabo | G06F 16/2457 |
| 2008/0140603 A1* | 6/2008 | Babikov | G06F 16/289 |
| | | | 706/59 |
| 2008/0154873 A1* | 6/2008 | Redlich | G06F 16/2425 |
| 2008/0155652 A1* | 6/2008 | DeBie | G06F 21/604 |
| | | | 726/2 |
| 2008/0168135 A1* | 7/2008 | Redlich | G06F 21/6218 |
| | | | 709/204 |
| 2009/0076839 A1* | 3/2009 | Abraham-Fuchs | G16H 70/60 |
| | | | 705/2 |
| 2009/0254572 A1* | 10/2009 | Redlich | G06Q 10/06 |
| 2010/0010968 A1* | 1/2010 | Redlich | G06Q 10/00 |
| | | | 707/E17.014 |
| 2010/0030734 A1* | 2/2010 | Chunilal | G06Q 10/10 |
| | | | 707/770 |
| 2013/0115927 A1 | 5/2013 | Gruber | |
| 2013/0132109 A1* | 5/2013 | Mruthyunjaya | G16H 70/60 |
| | | | 705/2 |
| 2014/0040714 A1* | 2/2014 | Siegel | G06F 16/93 |
| | | | 715/203 |
| 2015/0149491 A1* | 5/2015 | Redlich | G06F 16/23 |
| | | | 707/755 |
| 2015/0199410 A1 | 7/2015 | Redlich | |
| 2015/0242940 A1 | 8/2015 | Cockcroft | |
| 2015/0262105 A1* | 9/2015 | Jeffries | G06Q 30/018 |
| | | | 705/7.26 |
| 2016/0132648 A1* | 5/2016 | Shah | G16H 70/20 |
| | | | 705/2 |
| 2016/0275453 A1* | 9/2016 | Powers | G06F 3/04817 |
| 2016/0379270 A1 | 12/2016 | Shah | |
| 2017/0011046 A1* | 1/2017 | Kapoor | G06F 3/0481 |
| 2017/0034305 A1* | 2/2017 | Blevins | H04L 67/20 |
| 2017/0103167 A1* | 4/2017 | Shah | G16H 10/60 |
| 2017/0300634 A1* | 10/2017 | Chiang | G16H 10/60 |
| 2018/0300481 A1 | 10/2018 | Parinov | |
| 2019/0286819 A1 | 9/2019 | Maisel | |
| 2019/0287018 A1* | 9/2019 | Coupe | G06N 20/20 |

* cited by examiner

METHODS FOR PROVIDING USERS WITH ACCESS TO DATA USING ADAPTABLE TAXONOMIES AND GUIDED FLOWS

FIELD OF INVENTION

The field relates to complex information systems and, more specifically, to systems and methods for creating dynamic and adaptable taxonomies to classify data in such complex information systems in order to facilitate user navigation to data.

BACKGROUND OF THE DISCLOSURE

Complex information systems are information systems that include massive volumes of information, often extending into thousands or millions of files, and often addressing highly varied topics. However, such complex information systems present unique problems in information systems for users who seek to navigate through them. Resultantly, these complex information systems present problems for parties seeking to facilitate such navigation by users.

These problems are further exacerbated when complex information systems include related, similar, or overlapping domains and files. A consequence is that a user seeking to search for a particular file or within a particular domain may unknowingly arrive at information that does not match the actual needs of the user. These problems are made even more difficult when users are naïve or inexperienced with searching. Such users frequently do not understand how to identify pertinent search terms to find relevant files. Further, when naïve or inexperienced users obtain search results, the problem of overlapping and related domains may lead a user to mistakenly believe that they have identified pertinent information when a more pertinent, useful file is available.

As a result, these problems are particularly significant in situations where large volumes of inexperienced or naïve users are searching or browsing through files or information in complex information systems in order to identify important information. One notable example of this situation is in the context of information regarding healthcare services and providers. Typical users may have limited or no familiarity with underlying and complex domains regarding medicine and healthcare services. Yet, typical users seeking healthcare services may need to navigate through information systems with enormous bodies of files and information. These information systems may include many types of information that are varyingly complex and overlapping. Further, such information may include esoteric or complex terminology that may make effective searching difficult for users with limited familiarity with such terminology.

Although organization of data has been considered to address the problem of unstructured information systems, known systems for classifying and organizing information are insufficient to resolve these issues. Such known systems are insufficient at least in part because they fail to address changing information because they are dependent on manual organizational steps or are otherwise unable to sufficiently adapt to changing information systems.

As such, systems and methods are desirable for dynamic and adaptable taxonomical classification of data used to facilitate user navigation through complex information systems.

BRIEF SUMMARY OF THE INVENTION

In one aspect, a classification computing system is provided. The classification computing system provides adaptable taxonomies to facilitate user navigation of complex information systems. The classification computing system includes an information server, a user computing device, and a classification computer. The information server includes a server memory and a server processor. The user computing device includes a device memory and a device processor. The classification computer is in communication with the information server and the user computing device. The classification computer includes a memory and a processor. The memory includes instructions encoded thereupon that are used to configure the processor to perform those instructions. The processor is configured to receive a collection of file indices from the information server. The processor is also configured to apply a taxonomical classification algorithm to the collection to generate a collection of classified file indices including taxonomical classifications. Classified file indices can be associated with at least one of the taxonomical classifications. In an example embodiment, each of the classified file indices is associated with at least one of the taxonomical classifications. The processor is further configured to apply a flow algorithm to the collection to generate at least one flow path used to provide a user access to a first subset of taxonomical classifications. A flow path can restrict access to at least a second subset of taxonomical classifications. The flow path is responsive to associated user input parameters. The processor is also configured to receive a user input parameter from the user computing device. The processor is additionally configured to provide the flow path associated with the user input parameter to the user computing device.

In another aspect, a classification computer is provided. The classification computer provides adaptable taxonomies to facilitate user navigation of complex information systems. The classification computer is in communication with an information server and a user computing device. The classification computer includes a memory and a processor. The memory includes instructions encoded thereupon that are used to configure the processor to perform those instructions. The processor is configured to receive a collection of file indices from the information server. The processor is also configured to apply a taxonomical classification algorithm to the collection to generate a collection of classified file indices including taxonomical classifications. The classified file indices can be associated with at least one of the taxonomical classifications. In an example embodiment, each of the classified file indices is associated with at least one of the taxonomical classifications. The processor is further configured to apply a flow algorithm to the collection to generate at least one flow path used to provide a user access to a first subset of taxonomical classifications. The flow path can restrict access to at least a second subset of taxonomical classifications. In an example embodiment, each flow path restricts access to at least a second subset of taxonomical classifications. The flow path can be responsive to associated user input parameters. In an example, embodiment, each flow path is responsive to associated user input parameters. The processor is also configured to receive a user input parameter from the user computing device. The processor is additionally configured to provide the flow path associated with the user input parameter to the user computing device.

In yet another aspect, a method is provided for providing adaptable taxonomies to facilitate user navigation of complex information systems. The method is performed by a classification computer. The classification computer is in communication with an information server and a user computing device, and the classification computer includes a memory and a processor. The memory includes instructions encoded thereupon that are used to configure the processor to perform the instructions of the method. The method includes receiving a collection of file indices from the information server. The method also includes applying a taxonomical classification algorithm to the collection to generate a collection of classified file indices including taxonomical classifications. The classified file indices can be associated with at least one of the taxonomical classifications. In an example embodiment, each of the classified file indices is associated with at least one of the taxonomical classifications. The method also includes applying a flow algorithm to the collection to generate at least one flow path used to provide a user access to a first subset of taxonomical classifications. The flow path can restrict access to at least a second subset of taxonomical classifications. In an example embodiment, each flow path restricts access to at least a second subset of taxonomical classifications. The flow path can be responsive to associated user input parameters. In an example embodiment, each flow path is responsive to associated user input parameters. The method also includes receiving a user input parameter from the user computing device. The method additionally includes providing the flow path associated with the user input parameter to the user computing device.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein.

DETAILED DESCRIPTION

Figure 1:
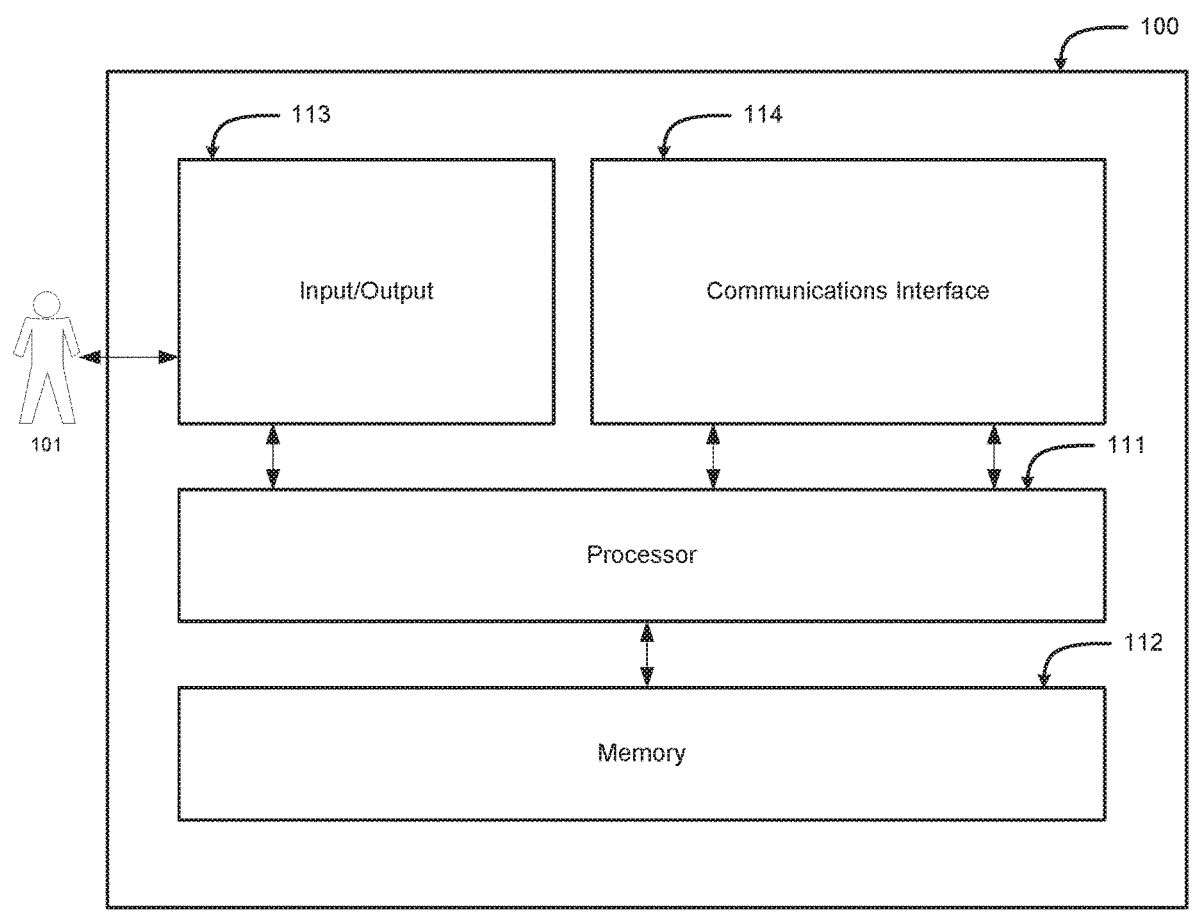
FIG. 1 is a functional block diagram of an example computing device that may be used in the environments described herein.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

As used herein, "complex information systems" refer to computing systems that are used to serve files, media, and other forms of information to end users. Complex information systems include all computing systems involved in the process of serving and receiving such information. Typically, and as used herein, complex information systems include at least an information server that provides information and a user computing device that receives information. In many examples, including those described herein, the information server provides information indirectly to user computing devices through secondary servers including processing servers, media servers, documents servers, and file servers. In other examples, the information server provides information directly to user computing devices. Information servers may include servers, mainframes, desktops, laptops, or any other computing device that is capable of providing user computing systems with access to such information. User computing devices may include any suitable computing device for receiving and presenting information including, without limitation, laptops, desktops, smartphones, and mobile computing devices. As described herein, the various computing systems of complex information systems are in networked communication using any suitable networking protocol including wired or wireless networking protocols. For ease of explanation, the description below is provided in the context of a primary example of a complex healthcare information system. The example complex healthcare information system is configured to provide users with a variety of healthcare information. The healthcare information ranges from medical services descriptions and information to billing and insurance information to healthcare provider information to specific details about individual procedures and services.

As used herein, "taxonomical classifications" refer to data structures to categorize information from information systems including complex information systems. Taxonomical classifications are therefore groups that contain information based on properties specific to the taxonomical classifications. In some examples, particular information may be categorized within multiple taxonomical classifications because such information is responsive to properties of more than one taxonomical classifications. Further, as described herein, taxonomical classifications may include sub-taxonomies or taxonomical sub-classifications. For example, a particular taxonomical classification X may contain taxonomical sub-classifications A, B, C, and D. While information in sub-classifications A, B, C, and D all contain common properties specific to classification X, sub-classifications A, B, C, and D each contain information with some properties specific to each sub-classification. Through application of increasingly granular taxonomical sub-classifications, the systems and methods described herein allow for organization of information in greater detail. Because the taxonomical classifications are responsive to the information contained therein, they may be described as dynamic and adaptable.

As used herein, "flows" refer to sequenced processing interfaces produced or displayed by machines in response to instructions that allow a user to access information that is relevant to the user. Specifically, flows are used in conjunction with taxonomical classifications to allow a user computing device to navigate through sub-classifications to particular information. The flows apply a tree-structure data model with conditional branching to direct users through taxonomical sub-classifications to particular information. The flows receive user input and apply the user input to the conditional branches to allow the user to access relevant information. Since sub-classifications for a particular taxonomical classification contain information with distinct properties for each sub-classification, the conditional branches provide a "flow" through the information in a taxonomical classification. For example, the flows may request information from a user computing device (e.g., by prompting the user computing device with a question, or by obtaining profile or location information from the user computing device) and use the responses to navigate through the conditional branches. As such, the flows are used in conjunction with the taxonomical classifications to provide user computing devices (and therefore users) with access to relevant information in complex information systems.

As described above, providing users with access to specific files or information is a known technological problem in complex information systems. Further, as described above, providing users access to such files or information is further complicated when the users are unsophisticated or unknowledgeable about the information contained within a particular complex information system. Because of the volume and complexity of the information in such complex information systems and the variety of the users accessing such information, it is typical for user computing devices to be unable to present appropriate information or files to users.

The systems and methods described herein address the technological problems identified above by use of a classification computing system that provides adaptable taxonomies that are used to classify and organize the information of the complex information systems. Further, the classification computing system uses such adaptable taxonomies to facilitate user navigation of the complex information systems to specific files or information. The classification computing system further applies a taxonomical classification algorithm to a collection of file indices in the information server and applies a flow algorithm to the collection to generate a set of "flows" (or flow paths). The classification computer also generates "guided flows" (or flow paths) which are dynamically generated navigation tools configured to allow certain users to access relevant information based on input provided by a user at a user computing device. The flow paths are served or provided to user computing devices based upon application of received user input parameters on the conditional branches of the flows. As such, the flow paths are specifically tailored to provide unsophisticated users with relevant information. Using these approaches, and other methods described herein, the systems and methods provided resolve known problems in computing technology, computing networks, and information systems by using specific technological solutions.

In the example embodiment, the methods described herein are performed by a classification computer within a classification computing system containing an information server and a user computing device. The classification computer is configured to receive a collection of file indices from the information server. As used herein, "files" may refer to any set of distinct files or information including, for example, web pages, text-based files, images, multimedia files, video files, audio files, applications, and interactive materials. As described herein, "indices" are any suitable identifiers that may be used to identify the location of underlying files within the information server, or in another location where the files are stored. In other words, the classification computer receives a collection of file indices that may be used to identify the locations each file of an associated collection of files within the classification computing system including, for example, within the information server. As used herein, the collection of file indices may be for any suitable amount of files within a complex information system including collection sizes exceeding millions, tens of millions, or hundreds of millions of indices.

The classification computer applies a taxonomical classification algorithm to the collection to generate a collection of classified file indices including taxonomical classifications. Each of the classified file indices is associated with at least one of the plurality of taxonomical classifications. In other words, the classification computer applies the taxonomical classification algorithm to organize the classified file indices within taxonomical classifications. In some examples, particular classified file indices may be present within multiple taxonomical classifications. As a result, in the systems and methods described, a particular file may be accessible to users within multiple taxonomical classifications.

In some examples, the classification computer applies the classification algorithm to determine and generate taxonomical classifications. The classification computer performs this function by processing all files associated with the collection of file indices to determine common properties (or features) that are present within more than one file. If common properties are present in multiple files, the classification algorithm determines a taxonomical classification (or category) to contain files with such properties. The taxonomical classification properties described herein correspond to such common properties. The classification algorithm may therefore process the files to identify, for example, common keywords, common metadata, and common location information. In some examples, the classification computer identifies taxonomical sub-classifications that have a set of classification properties that define a higher level of taxonomical classification as well as additional classification properties. Such taxonomical sub-classifications therefore have more specific criteria than the higher level taxonomical classification and are "lower" within the same hierarchy. The classification computer is configured to identify and organize the taxonomical classifications and taxonomical sub-classifications in a hierarchical manner to determine an adaptable taxonomy. In the example embodiment, the classification computer identifies each taxonomical classification and performs a comparison of the classification properties associated with each taxonomical classification. For example, a particular taxonomical classification X may include classification properties AA, BB, CC, and DD. The classification computer may identify taxonomical classification Y and determine that it includes classification properties AA, BB, CC, DD, and EE. Because taxonomical classification Y includes all classification properties that define taxonomical classification X, and thereby satisfies its criteria, taxonomical classification Y is determined to be a sub-classification and a "child" of taxonomical classification X. Likewise, where the classification properties of two taxonomical classifications are distinct (i.e., neither is a subset of the other), the classification computer is configured to categorize the two taxonomical classifications as distinct from one another.

The classification algorithm analyzes the files associated with the file indices to identify which taxonomical classification properties (or category properties) to which they correspond. As explained above, taxonomical classification properties are attributes that may be used to associate a particular file (identified by a file index) within a taxonomical classification. The classification algorithm is configured to identify all classification properties present within each of the files and to associate each file with a corresponding taxonomical classification or taxonomical classifications that are defined by the same classification properties.

In one example, taxonomical classification properties may be further distinguished by their respective property types. Taxonomical classification property types may include, for example, keywords, metadata attributes, owner, publisher, location, relevant demographic, and relevant user characteristics. For ease of explanation, examples of taxonomical classification property types are described below in the context of complex healthcare information systems.

Keywords may include terms, phrases, and other text that is present in a particular file. In the specific context of the given example of complex healthcare information systems, keywords may relate to descriptions of healthcare services. For example, the keywords "primary care", "pcp doctor" and "primary doctor" are keywords that may be used to classify files containing some or all of them with the taxonomical classifications of "PCP", "providers", or "PCP procedures". Similarly, "back doctor", "spine doctor", "lower back doctor", or "sciatica" are keywords that may be used to classify files containing some or all of them with the taxonomical classifications of "back doctor" or "orthopedics". To continue the example, "dentist", "tooth doctor", "dental cleaning", and "regular dentist", are keywords that may be used to classify files containing some or all of them with the taxonomical classifications of "general dentist procedures" or "dentist providers". Thus, in the examples where taxonomical classification property types are keywords, the classification algorithm analyzes the files identified by the collection of file indices to determine which files contain which keywords.

Taxonomical classification property types may also include metadata associated with each file, thereby allowing for taxonomical classifications to be determined based on shared metadata between files. Such shared metadata may include any suitable metadata such as, for example, file creation date, file creation month, file creation year, file author, file location (i.e., where a file is stored within the complex information system), file type, file language, and file description.

In some examples, files may be particularly relevant to particular types of users or users in particular locations or particular networks. For example, in the example of a complex healthcare information system, particular files may be more relevant to users based on their demographics, their physical location, their insurance networks, or other factors. For instance, a user computing device may include a user profile that identifies demographic attributes of a patient, such as gender or age. Depending on such information, certain files may be unlikely to be relevant to a user. For example, a user over ninety years of age may be interested in files related to geriatric care while a user of twenty-five years of age is less likely to be so interested. Similarly, a female adult patient seeking information on annual checkups may be interested in files related to an OB/GYN checkup while a male patient is less likely to be so interested. Further, a patient is more likely to be interested in files related to services provided in her geographic region or within her insurance network than those that are not. As a result, the classification algorithm is configured to determine taxonomical classification properties (and taxonomical classifications) related to whether particular files are responsive to user profiles with particular demographics, locations, or insurance networks.

In some examples, including the above, the systems and methods use user information (such as information contained in user profiles) to classify files and to identify responsive files. When user information is used, the systems and methods described herein are designed to ensure that the patient data is kept secure, private, and confidential as necessary according to any appropriate regulations or laws including the Health Insurance Portability and Accountability Act (HIPAA).

Taxonomical classification properties may also be associated with multiple levels of taxonomical classifications. For example, the keywords "physical", "medical checkup", "back X-ray", and "spine MM" may all be associated with the taxonomical classification of "procedures". However, the keywords "back X-ray" and "spine MRI" are associated with the taxonomical classification of "back imaging" while the keywords "physical" and "medical checkup" are not. Similarly, the keywords "physical" and "medical checkup" are associated with the taxonomical classification of "annual physical" while the keywords "back X-ray" and "spine MRI" are not. As such, distinct taxonomical classifications may include overlapping files.

Taxonomical classification properties are also associated with "flows". As described below and herein, flows allow a user to access information that is relevant to the user. Specifically, the flows are sequenced processing interfaces that receive user input parameters and identify responsive information based on such parameters. The flows are designed with a tree structure that provides access for users to lower branches containing increasingly narrow selections of information. Access to lower branches is provided based on the application of user input parameters to the conditional branches. In some examples, the user input parameters refer to information directly elicited from a user by sending a request (and receiving a response) to a user computing device to answer a particular prompt. In other examples, the user input parameters refer to information obtained passively from a user via, for example, user profile information obtained from a user computing device or location information obtained from a user computing device. As such, in some examples, the flows provide user computing devices with prompts including questions. The flows are configured to receive responses from the user computing devices to those questions and to direct the user computing device to a next (lower) level of the flow until the user obtains relevant files (or information). In the context of the complex healthcare information system, a user may select options to identify desired healthcare services until obtaining specific information for a desired healthcare service such as a billing code, a provider name, a provider contact information, insurer information, service descriptions, or service costs.

Accordingly, the classification computer is configured to apply a flow algorithm to the collection to generate at least one flow path used to provide a user access to a first subset of taxonomical classifications. In an example embodiment, each path provides user computing devices (and users) with restricted access to taxonomical classifications (and sub-classifications) depending on the user input parameters provided actively or passively. Because of the increasing restriction, each flow path restricts access to at least a second subset of taxonomical classifications. Further, each flow path is responsive to associated user input parameters provided actively or passively.

The classification computer is also configured to receive user input parameters, directly or indirectly, from the user computing device. As explained above and herein, user input parameters may be received in any suitable form including actively as keywords, a search query, or as a response from the user computing device to a prompt. User input parameters may also be obtained passively from a user computing device such as by obtaining from the user computing device user profile information (that describes the user) or user computing device profile information (that describes the user computing device). The user profile may include, for example, any user information including user identifiers, user demographic information, user insurance information, user medical history, and user medical information. Information obtained from a user computing device profile may include, for example, device location, device type, device software type, device media settings, and device localization settings.

The classification computer is also configured to apply the user input parameters and provide the flow path associated with the user input parameter to the user computing device.

In one example, the classification computer applies the flow algorithm to the collection to generate the at least one flow path, such that each flow path includes at least one conditional branch. In other words, access to each flow path is provided based on whether a condition is satisfied by user input parameters. The classification computer accordingly provides the flow path associated with the user input parameter to the user computing device such that the flow path is provided with the at least one conditional branch. As the user navigates down the flow path (or a set of flow paths), the classification computer identifies a responsive file included within the first subset of taxonomical classifications by applying the user input parameter to the flow path and the at least one conditional branch. The classification computer also provides the responsive file to the user computing device.

Effectively, the adaptable taxonomies and flow path provide distinct organization to the complex information system that allows a user computing device to initially navigate to a taxonomical classification based on a user input parameter such as a keyword search or a user profile. The user computing device then is provided access to taxonomical sub-classifications (children of the initially provided parent taxonomical classification) based on further user input parameters.

In some cases, such navigation to taxonomical sub-classifications is performed using a "guided flow" while in others a user navigates without a "guide" by providing input. A "guided flow" is a flow where a user is presented with particular questions directed to assist the user in providing relevant user input parameters to navigate to lower branches, lower taxonomical sub-classifications, and to a responsive file. In some examples, the classification computer is configured to generate a user prompt based on the at least one conditional branch and provide the user prompt to the user computing device. In other words, to distinguish between two sub-classifications, the classification computer may prompt a user computing device to determine which branch is appropriate. For example, if a user computing device has navigated to a taxonomical sub-classification related to general dentistry services, the classification computer may prompt the user to select whether they are interested in an initial visit, a cleaning and checkup, cavity treatment, or a root canal. The classification computer receives a prompt response in response to the user prompt from the user computing device integrates the prompt response into the user input parameter. As such, the classification computer may receive input (identifying that the user is interested in cavity treatment, for example) and incorporate that input into the user input parameters for navigation to a lower level of the taxonomical sub-classifications to eventually obtain a responsive file.

In some cases, information may never be appropriate or pertinent to a user because of user characteristics. For example, in the context of complex healthcare information systems, geographic or insurer attributes may restrict the applicability or availability of certain healthcare services. As such, files and information related to such services may be appropriately screened out from the user computing device. The classification computer may receive a user screen input associated with the user computing device. The user screen defines a set of information to not serve to the user computing device. As such, the classification computer applies the user screen input to the at least one flow path to generate at least one screened flow path used to provide a user access to a screened portion of the first subset of taxonomical classifications that does not include the set of information to not serve to the user computing device. Each screened flow path restricts access to at least the second subset of taxonomical classifications. Each screened flow path is responsive to the associated user input parameters.

In some examples, the classification computer is configured to refactor, enhance, or increase the scope and depth of the adaptable taxonomies on a periodic basis or on a continual basis. Such refactoring, enhancement, and increased scope and depth are provided in order to support additional use cases for users navigating the complex information system to access data. As such, the taxonomical classification algorithm and the flow algorithm may be periodically or continually updated. In other examples, the underlying data of the complex information system may periodically or continually change. As such, the taxonomical classification algorithm and the flow algorithm may be routinely re-executed in order to address the changing and dynamic nature of the information in the complex information system. As used herein, refactoring is a change in weighting of factors used to determine the path through a guided search flow. As used herein, enhancement refers to the refining of an existing input to define taxonomies or a flow path. As used herein, increasing the scope refers to adding new taxonomical classifications and new paths from an existing flow paths. As used herein, increasing depth refers to creating lower levels within a taxonomy based on the information of the healthcare information system, and increased flow paths within such taxonomies.

The described use cases are presented for illustrative purposes. In other examples, other use cases of the systems and methods described herein may be provided by combining or adapting any of the described steps.

Generally, the systems and methods described herein are configured to perform at least the following steps that may be performed in any order, and using any permutation of such steps: receive a collection of file indices from the information server; apply a taxonomical classification algorithm to the collection to generate a collection of classified file indices including a plurality of taxonomical classifications, wherein each of the classified file indices is associated with at least one of the plurality of taxonomical classifications; apply a flow algorithm to the collection to generate at least one flow path used to provide a user access to a first subset of taxonomical classifications, wherein each at least one flow path restricts access to at least a second subset of taxonomical classifications, each at least one flow path responsive to associated user input parameters; receive a user input parameter from the user computing device; provide the flow path associated with the user input parameter to the user computing device; apply the flow algorithm to the collection to generate the at least one flow path, wherein the at least one flow path includes at least one conditional branch; provide the flow path associated with the user input parameter to the user computing device, wherein the flow path is provided with the at least one conditional branch;

identify a responsive file included within the first subset of taxonomical classifications by applying the user input parameter to the flow path and the at least one conditional branch; provide the responsive file to the user computing device; generate a user prompt based on the at least one conditional branch; provide the user prompt to the user computing device; receive a prompt response in response to the user prompt from the user computing device; integrate the prompt response into the user input parameter; receive a user screen input associated with the user computing device, wherein the user screen defines a set of information to not serve to the user computing device; apply the user screen input to the at least one flow path to generate at least one screened flow path used to provide a user access to a screened portion of the first subset of taxonomical classifications that does not include the set of information to not serve to the user computing device, wherein each at least one screened flow path restricts access to at least the second subset of taxonomical classifications, each at least one screened flow path responsive to associated user input parameters; receive the user input parameter from the user computing device, wherein the user input parameters comprise a search query; receive the user input parameters from the user computing device, wherein the user input parameters comprise a user profile including at least one of user demographics and user medical information; receive the user input parameter from the user computing device wherein the user input parameter includes a geographic location of the user computing device; and provide the flow path associated with the geographic location to the user computing device.

FIG. 1 is a functional block diagram of an example computing device 100 that may be used in the environments described herein. Specifically, computing device 100 illustrates an exemplary configuration of a computing device. Computing device 100 illustrates an exemplary configuration of a computing device operated by a user 101 in accordance with one embodiment of the present invention. Computing device 100 may include, but is not limited to, a classification computer, an information server, a user computing device, and a storage management device, and any other system described herein. Computing device 100 may also include information servers and processors used in complex information systems, healthcare information servers, healthcare network servers, mobile computing devices, stationary computing devices, computing peripheral devices, smart phones, wearable computing devices, medical computing devices, and vehicular computing devices. Alternatively, computing device 100 may be any computing device capable of providing adaptable taxonomies to facilitate user navigation of complex information systems, as described herein. In some variations, the characteristics of the described components may be more or less advanced, primitive, or non-functional.

In the exemplary embodiment, computing device 100 includes a processor 111 for executing instructions. In some embodiments, executable instructions are stored in a memory area 112. Processor 111 may include one or more processing units, for example, a multi-core configuration. Memory area 112 is any device allowing information such as executable instructions and/or written works to be stored and retrieved. Memory area 112 may include one or more computer readable media.

Computing device 100 also includes at least one input/output component 113 for receiving information from and providing information to user 101. In some examples, input/output component 113 may be of limited functionality or non-functional as in the case of some wearable computing devices. In other examples, input/output component 113 is any component capable of conveying information to or receiving information from user 101. In some embodiments, input/output component 113 includes an output adapter such as a video adapter and/or an audio adapter. Input/output component 113 may alternatively include an output device such as a display device, a liquid crystal display (LCD), organic light emitting diode (OLED) display, or "electronic ink" display, or an audio output device, a speaker or headphones. Input/output component 113 may also include any devices, modules, or structures for receiving input from user 101. Input/output component 113 may therefore include, for example, a keyboard, a pointing device, a mouse, a stylus, a touch sensitive panel, a touch pad, a touch screen, a gyroscope, an accelerometer, a position detector, or an audio input device. A single component such as a touch screen may function as both an output and input device of input/output component 113. Input/output component 113 may further include multiple sub-components for carrying out input and output functions.

Computing device 100 may also include a communications interface 114, which may be communicatively couplable to a remote device such as a remote computing device, a remote server, or any other suitable system. Communication interface 114 may include, for example, a wired or wireless network adapter or a wireless data transceiver for use with a mobile phone network, Global System for Mobile communications (GSM), 3G, 4G, or other mobile data network or Worldwide Interoperability for Microwave Access (WIMAX). Communications interface 114 is configured to allow computing device 100 to interface with any other computing device or network using an appropriate wireless or wired communications protocol such as, without limitation, BLUETOOTH®, Ethernet, or IEE 802.11. Communications interface 114 allows computing device 100 to communicate with any other computing devices with which it is in communication or connection.

Figure 2:
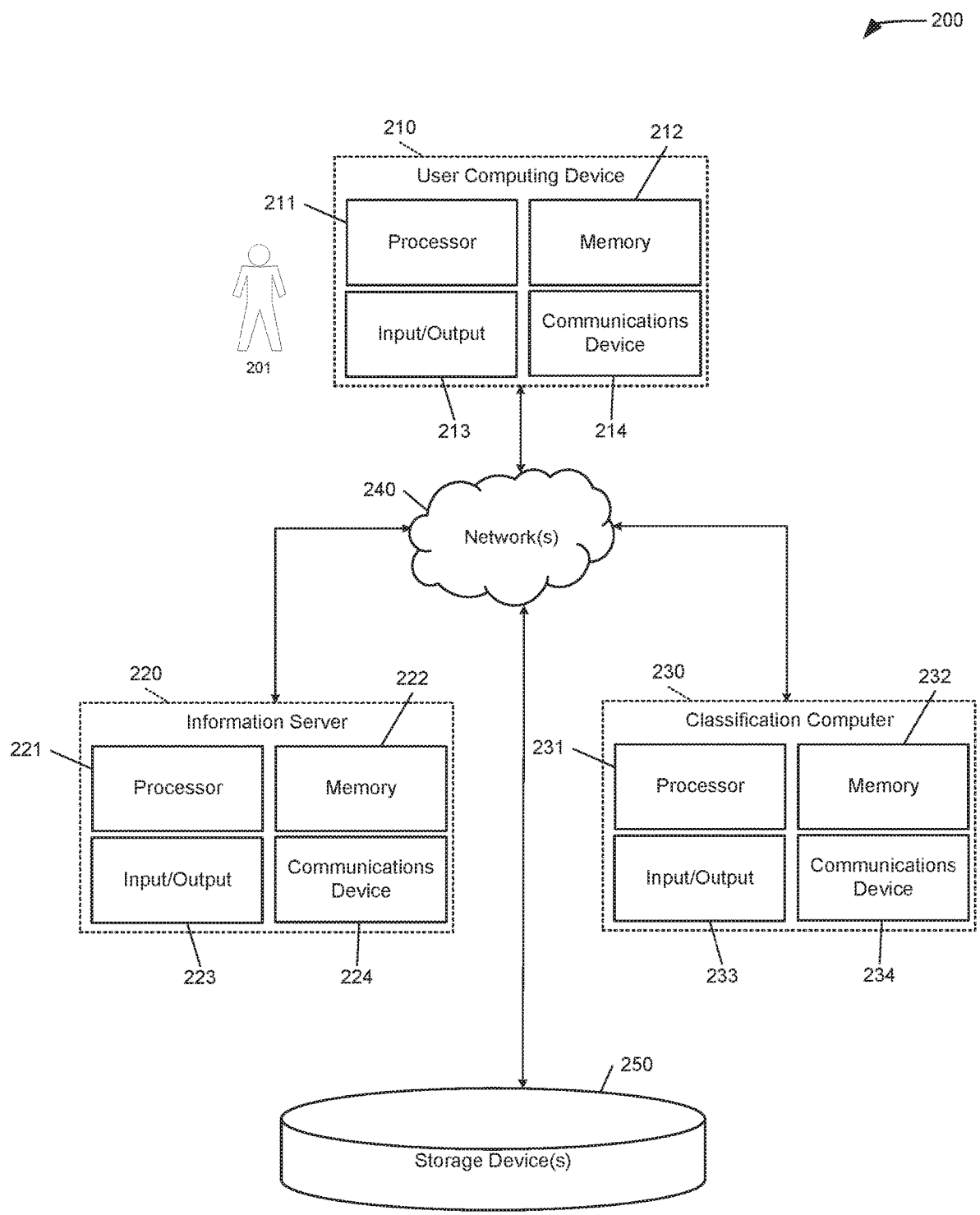
FIG. 2 is a functional block diagram of a classification computing system for providing adaptable taxonomies to facilitate user navigation of complex information systems, including a classification computer, an information server, and a user computing device.

FIG. 2 is a functional block diagram of a classification computing system 200 for providing adaptable taxonomies to facilitate user navigation of complex information systems, including a classification computer 230, an information server 220, and a user computing device 210. The devices 210, 220, and 230 of classification computing system 200 function in a manner similar to computing device 100 (shown in FIG. 1) and accordingly have the same or similar capabilities including processors 211, 221, and 231, memories 212, 222, and 232, input/outputs 213, 223, 233, and communications devices 214, 224, and 234. Devices 210, 220, and 230 are in communication with one another through network 240. Devices 210, 220, and 230 also may access externally stored information from external storage devices 250.

In the example embodiment, user 201 accesses user computing device 210 to access the information provided by the complex information system reflected in classification computing system 200. As such, user 201 accesses user computing device 210 to navigate through interfaces facilitated and provided by classification computer 230 (and more specifically the adaptable taxonomies and flows provided thereby) to responsive files.

Figure 3:
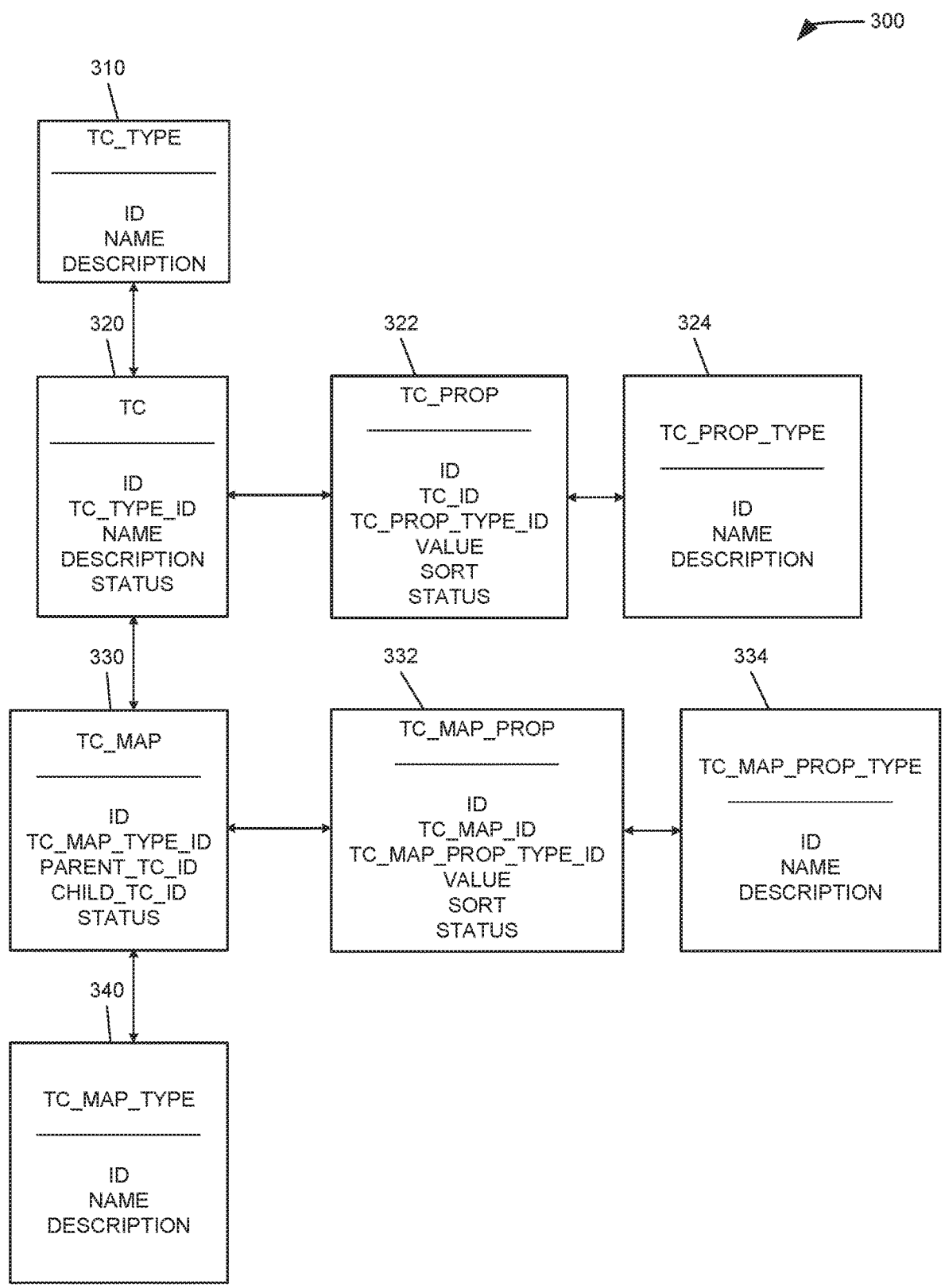
FIG. 3 is an exemplary schematic diagram used by the classification computer of FIG. 2 to create adaptable taxonomies to facilitate user navigation of complex information systems.

FIG. 3 is an exemplary schema 300 used by classification computer 230 (shown in FIG. 2) to create adaptable taxonomies to facilitate user navigation of complex information systems. Specifically, schema 300 describes internal relationships used in defining the adaptable taxonomies and, more particularly, the relationships between taxonomical classification types 310, taxonomical classifications 320, taxonomical classifications properties 322, taxonomical classification property types 324, taxonomical classification maps 330, taxonomical classification map properties 332, taxonomical classification map property types 334, and taxonomical classification map types 340.

Schema 300 defines data layouts for each of data elements 310, 320, 322, 324, 330, 332, 334, and 340. Each of data elements 310, 320, 322, 324, 330, 332, 334, and 340 are designed to access other elements using identifiers and the relationships shown. The data layouts for these elements are exemplary and in operation suitable alternatives may be used to provide the adaptable taxonomies described. Taxonomical classifications 320 are associated with taxonomical classification types 310. Specifically, taxonomical classification types 310 identify characteristics of a taxonomical classification 320 other than the hierarchical location, property, or property type of taxonomical classification 320. Taxonomical classification types 310 are associated with an identifier (ID), a name (NAME), and a description (DESCRIPTION). Taxonomical classifications 320 are each associated with a taxonomical classification type identification (TC_TYPE_ID) that corresponds to the identification (TYPE_ID) of taxonomical classification types 310. Taxonomical classifications 320 further directly relate to taxonomical classification properties 322 and taxonomical classification map 330. As described above and herein, taxonomical classification properties 322 are the elements that define each taxonomical classification 320 and provide commonality across the files or information contained therein. Taxonomical classification map 330 provides hierarchical structure to taxonomical classifications 320 and allows for the generation of adaptable taxonomies with taxonomical classifications acting as parents to taxonomical sub-classification children. Taxonomical classifications 320 are defined by an identifier (ID), taxonomical classification type identifier (TC_TYPE_ID) referencing taxonomical classification type 310, a name (NAME), a description (DESCRIPTION), and a status (STATUS). Taxonomical classification properties 322 relate directly to both taxonomical classifications 320 and taxonomical classification property types 324. As described above and herein, taxonomical classification properties 322 are the elements that define each taxonomical classification 320 such as, for example, keywords, metadata attributes, owner, publisher, location, relevant demographic, and relevant user characteristics associated with a particular taxonomical classification 320. Taxonomical classification properties 322 are defined by an identifier (ID), a taxonomical classification identifier (TC_ID) referencing taxonomical classification 320, a taxonomical classification property type identifier (TC_PROP_TYPE_ID) referencing taxonomical classification property type 324, a value (i.e., the value associated with the given property), a sort (i.e., how the data is sorted), and a status. Taxonomical classification property types 324 are the elements that set out each type of taxonomical classification property 322 and define whether they are, for example, keywords, metadata attributes, owner, publisher, location, relevant demographic, or relevant user characteristics. Taxonomical classification property types 324 are defined by an identifier (ID), a name (NAME), and a description (DESCRIPTION).

Schema 300 also includes hierarchical definition elements 330, 332, 334, and 340 that are used to define the structural relationships of the adaptable taxonomies. The primary element to provide the structure is taxonomical classification map 330 that provides and defines parent-child relationships between taxonomical classifications 320. Taxonomical classification map 330 is defined by an identifier (ID), a taxonomical classification map type identifier (TC_MAP_TYPE_ID) referencing taxonomical classification map type 340, a parent taxonomical classification identifier (PARENT_TC_ID), a child taxonomical classification identifier (CHILD_TC_ID), and a status (STATUS). Taxonomical classification map properties 332 allow the definition of a taxonomical classification map 330 and are defined by an identifier (ID), a taxonomical classification map identifier (TC_MAP_ID) referencing taxonomical classification map 330, a taxonomical classification map property type identifier (TC_MAP_PROP_TYPE_ID) referencing taxonomical classification map property type 334, a value (i.e., any value associated with the taxonomical classification map property 332), a sort, and a status. Taxonomical classification map property type 334 allows for definition of each grouping or type of taxonomical classification map properties 332 and is defined by identifier (ID), name (NAME), and description (DESCRIPTION). Taxonomical classification map type 340 allows for further definition and flexibility in creating adaptable taxonomies by allowing for varying taxonomical classification map types 340 to be used for each taxonomical classification map 330.

FIGS. 4-9 are exemplary process diagrams 400, 500, 600, 700, 800, and 900 illustrating the use of the adaptable taxonomies and guided flows to facilitate user navigation of complex information systems. FIGS. 4-9 are exemplary and provided for ease of understanding. In process diagram 400, a high level view is provided to show how a user may navigate to relevant files (or information) based on unsophisticated inputs. In diagram 400, a user provides one of several exemplary keywords 411, 412, and 413 related to primary care that are associated with a taxonomical classification 410 for primary care physicians. Applying the approach of the schema of FIG. 3, in diagram 400 keywords 411, 412, and 413 are accordingly taxonomical classification properties 322 used to define taxonomical classification 320 (both shown in FIG. 3). Accordingly, a user input parameter is provided containing one of keywords 411, 412, and 413 which is identified by the classification computer 230 as related to taxonomical classification 410. The classification computer 230 also accesses a user computing device profile 422 that may contain information related to a user or a user computing device. If user computing device profile 422 is available, it may define age and gender attributes for a user. The user computing device profile 422 can provide information from a stored data record that is used as an input parameter to determine the taxonomical classification and used to select a flow path. In such an example, a user may be directed to an appropriate file for one of services 431, 432, 433, and 434. For example, if user computing device profile 422 identifies a user profile as being associated with a child, it may be used as a user input parameter for the classification computer 230 to determine that a flow path should be provided to a file for pediatrician service 432. Alternately, if user computing device profile 422 identifies a user profile as being associated with an elderly person, it may be used as a user input parameter for the classification computer 230 to determine that a flow path should be provided to a file for geriatric practice 433. Further, if user computing device profile 422 identifies a user profile as being associated with a female person, it may be used as a user input parameter for the classification computer 230 to determine that a prompt should be presented to determine if the user wishes to view a file for OB/GYN services 434 based on response to, for example, user prompt input 424. If none of these conditions applies, the classification computer 230 may determine that a flow path should be provided for a file for family practice 431.

Applying the approach of the schema of FIG. 3, in diagram 500 keywords 511, 512, and 513 are accordingly taxonomical classification properties 322 used to define taxonomical classifications 320 (both shown in FIG. 3). Accordingly, a user input parameter is provided containing one of keywords 511, 512, and 513 which is identified by the classification computer 230 as related to taxonomical classifications 521 and 522. Because in diagram 500, keywords 511, 512, and 513 are properties for two taxonomical classifications 521 and 522, classification computer 230 presents guided flow 510 to allow a user to determine which classification 521 or 522 is preferred. In diagram 500, presenting guided flow 510 includes presenting information and user interfaces to describe the services related to taxonomical classifications 521 (PCP services) and 522 (orthopedist services). Accordingly, as described herein, classification computer 230 is configured to present user interfaces and information in guided flows to allow a user to distinguish between such services. In the example embodiment, guided flow 510 explains the primary functions of orthopedists and primary care services along with associated costs and available providers.

Figure 4:
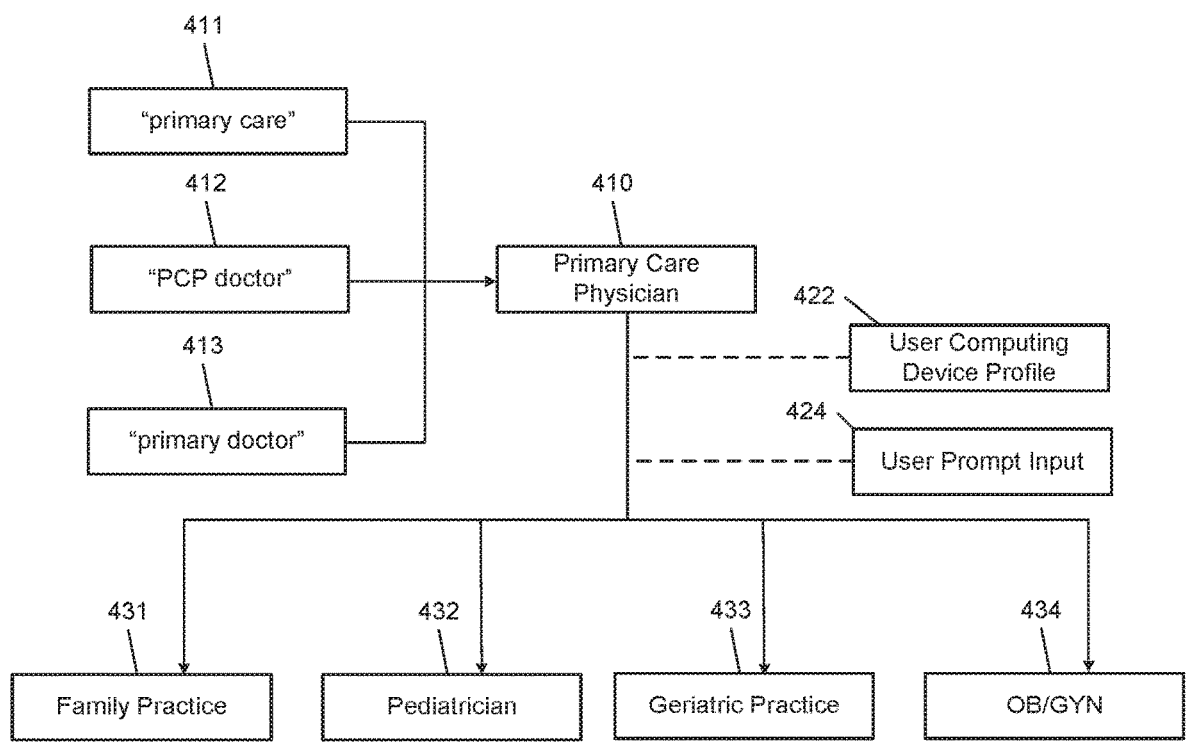
FIGS. 4-9 are exemplary process diagrams illustrating the use of the adaptable taxonomies and guided flows to facilitate user navigation of complex information systems.
Figure 5:
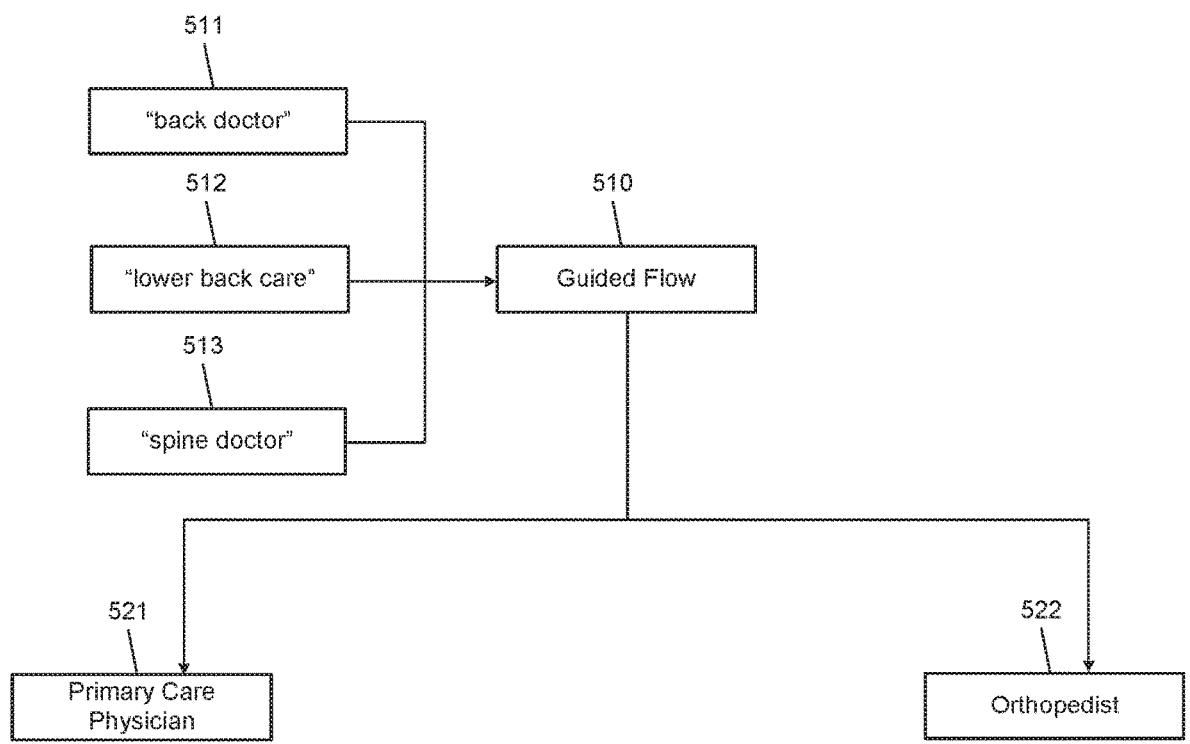
Figure 6:
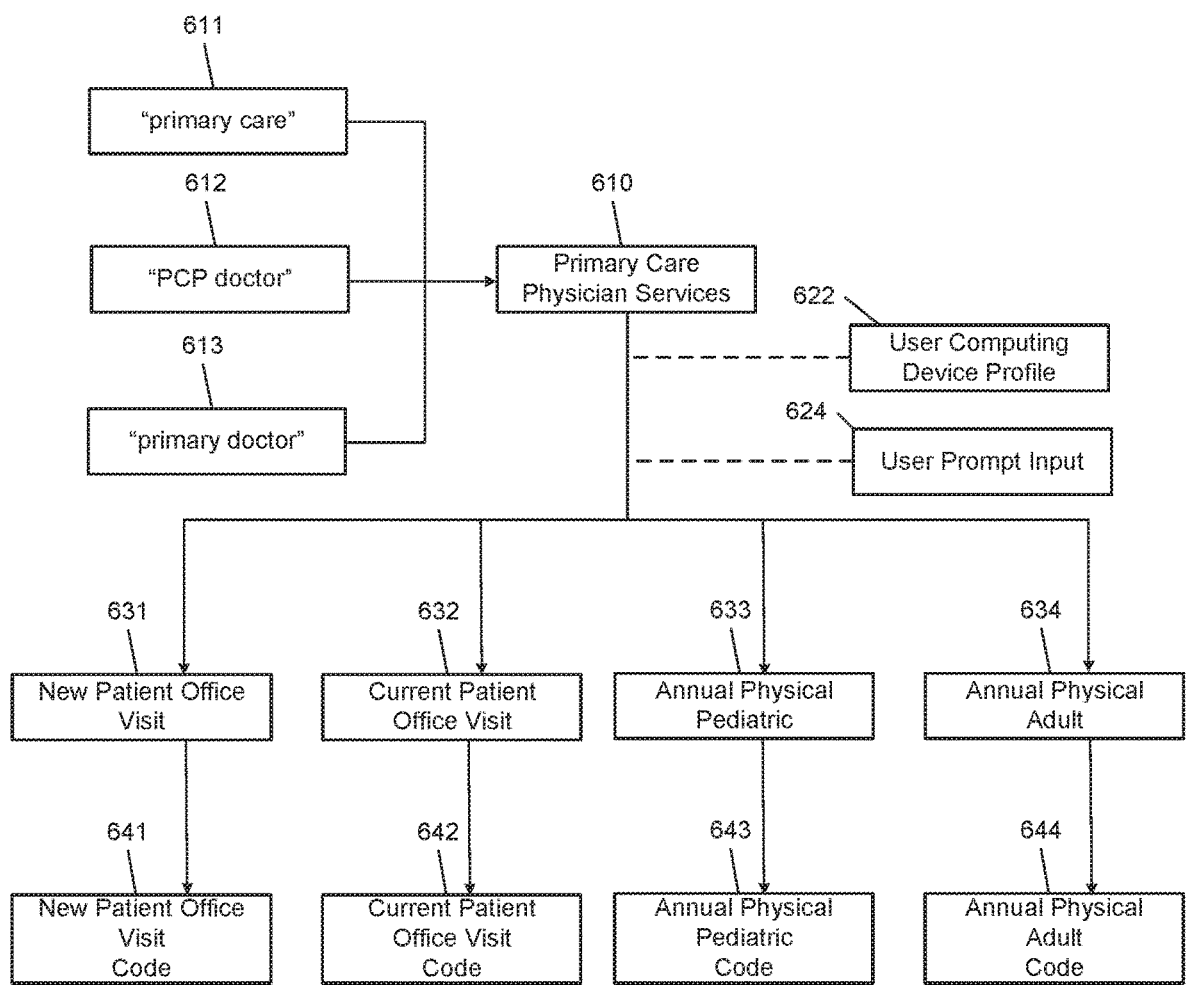

Compared to FIG. 4, FIG. 6 illustrates applying the approach of the schema of FIG. 3 to define taxonomical classification 610 and define sub-classifications for services 631, 632, 633, and 634 and associated service codes 641, 642, 643, and 644. Thus, while keywords 611, 612, and 613 are properties for the taxonomical classification of primary care physician services 610, there are also taxonomical sub-classifications 631, 632, 633, 634, 641, 642, 643, and 644 and it is not clear from the keywords which sub-classifications are appropriate. As in FIG. 4, user computing device profiles 622 or user prompt inputs 624 may be used to distinguish to which service 631, 632, 633, and 634 a user is directed by classification computer 230. For example, if user input parameters 622 or 624 indicate that a user is a new patient for a given clinic, classification computer 230 provides a flow path for new patient office visit 631 and new patient office visit service code 641. If user input parameters 622 or 624 indicate that a user is an existing patient for a given clinic and is not timely for an annual physical, classification computer 230 provides a flow path for current patient office visit 632 and current patient office visit service code 642. If user input parameters 622 or 624 indicate that a user is an existing patient for a given clinic and is timely for an annual physical and is under eighteen years of age, classification computer 230 provides a flow path for annual physical pediatric 632 and annual physical pediatric service code 642. If user input parameters 622 or 624 indicate that a user is an existing patient for a given clinic and is timely for an annual physical and is eighteen years of age or older, classification computer 230 provides a flow path for annual physical adult 632 and annual physical adult service code 642. Further, when classification computer 230 directs users to a flow for any of services 631, 632, 633, and 634, classification may further prompt if the user is interested in such services and interested in obtaining an associated code before providing associated service codes 641, 642, 643, and 644.

Figure 7:
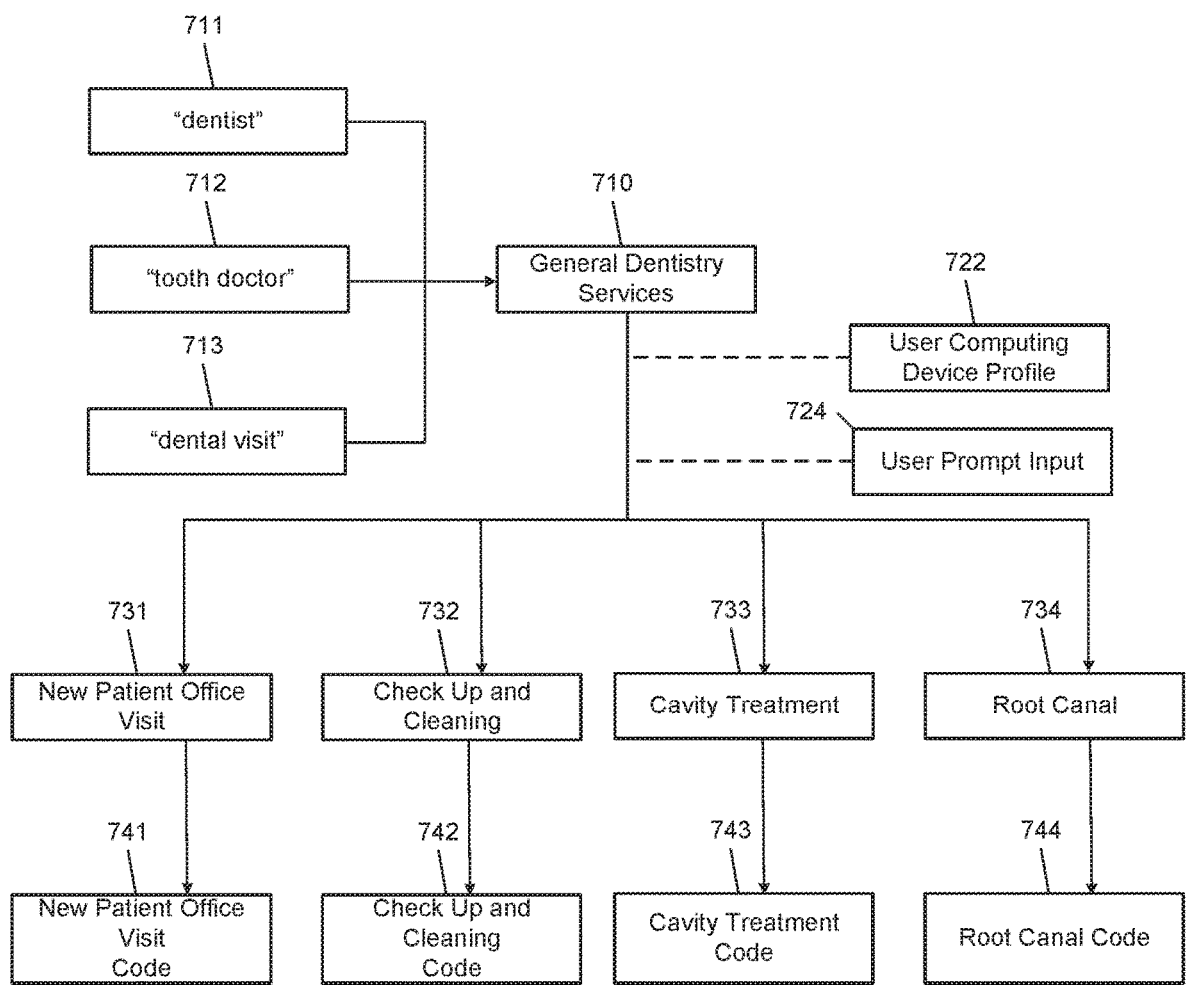

As in FIG. 6, FIG. 7 illustrates applying the approach of the schema of FIG. 3 to define taxonomical classification 710 and define sub-classifications for services 731, 732, 733, and 734 and associated service codes 741, 742, 743, and 744. Again, keywords 711, 712, and 713 are properties for the taxonomical classification of general dentistry services 710, and there are also taxonomical sub-classifications 731, 732, 733, 734, 741, 742, 743, and 744 and it is not clear from the keywords which sub-classifications are appropriate. As in FIGS. 4 and 6, user computing device profiles 722 or user prompt inputs 724 may be used to distinguish to which service 731, 732, 733, and 734 a user is directed by classification computer 230. For example, if user input parameters 722 or 724 indicate that a user is a new patient for a given clinic, classification computer 230 provides a flow path for new patient office visit 731 and new patient office visit service code 741. If user input parameters 722 or 724 indicate that a user is an existing patient for a given clinic and is not timely for a cleaning and checkup, classification computer 230 provides a flow path for current patient office visit 732 and current patient office visit service code 742. If neither condition applies, classification computer 230 generates a prompt to determine if cavity treatment services or root canals are requested and, if so, provides a flow path for cavity treatment 733 and cavity treatment code 743 or root canal 734 and root canal code 734. Further, when classification computer 230 directs users to a flow for any of services 731, 732, 733, and 734, classification may further prompt if the user is interested in such services and interested in obtaining an associated code before providing associated service codes 741, 742, 743, and 744.

Figure 8:
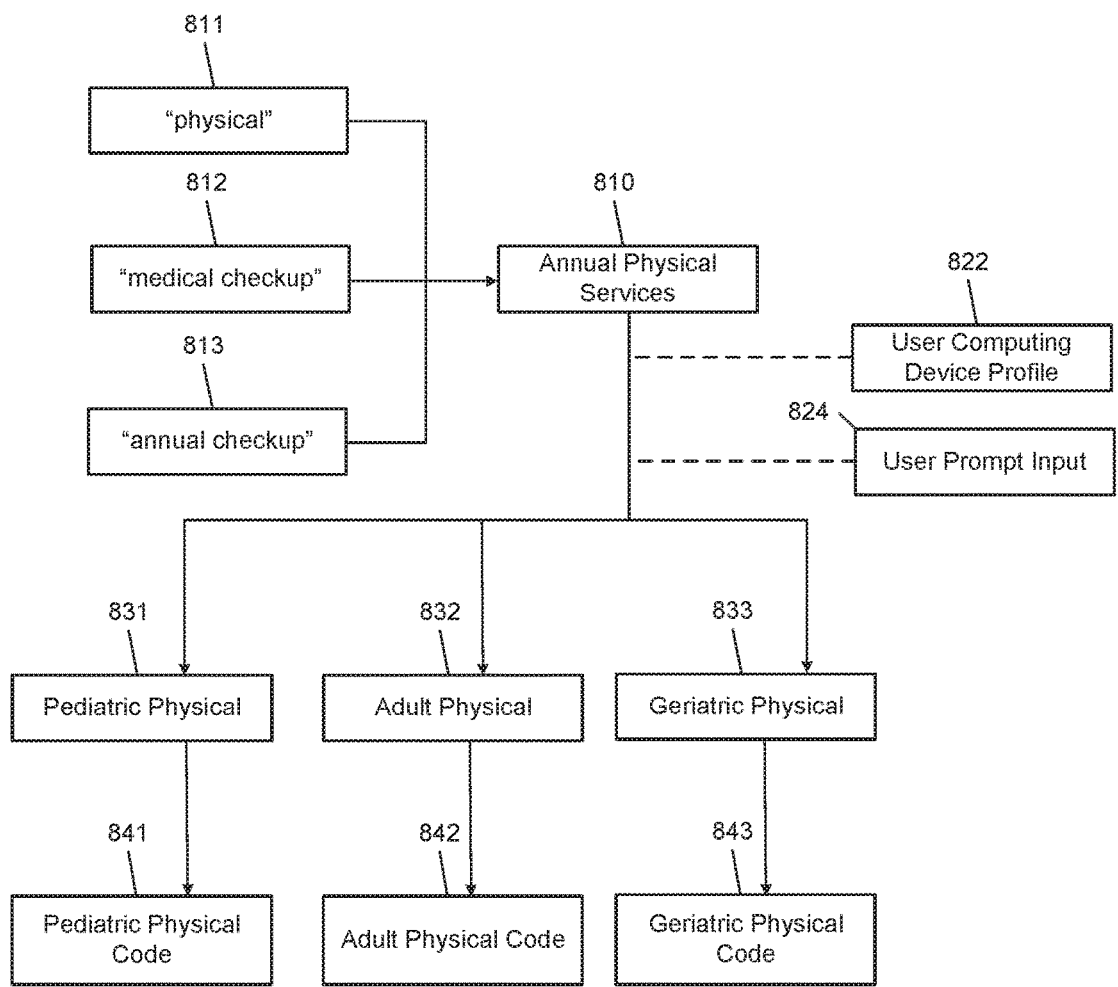

Compared to FIG. 4, FIG. 8 illustrates applying the approach of the schema of FIG. 3 to define taxonomical classification 810 and define sub-classifications for services 831, 832, and 833 and associated service codes 841, 842, and 843. Thus, while keywords 811, 812, and 813 are properties for the taxonomical classification of annual physical services 810, there are also taxonomical sub-classifications 831, 832, 833, 841, 842, and 843 and it is not clear from the keywords which sub-classifications are appropriate. As in FIGS. 4, 6, and 7, user computing device profiles 822 or user prompt inputs 824 may be used to distinguish to which service 831, 832, and 833 a user is directed by classification computer 230. For example, if user input parameters 822 or 824 indicate that a user is a under eighteen years of age, eighteen years of age or older, or an elderly person, classification computer 230 provides a flow to services 831, 832, or 833 respectively along with a flow to service codes 841, 842, or 843 respectively.

Figure 9:
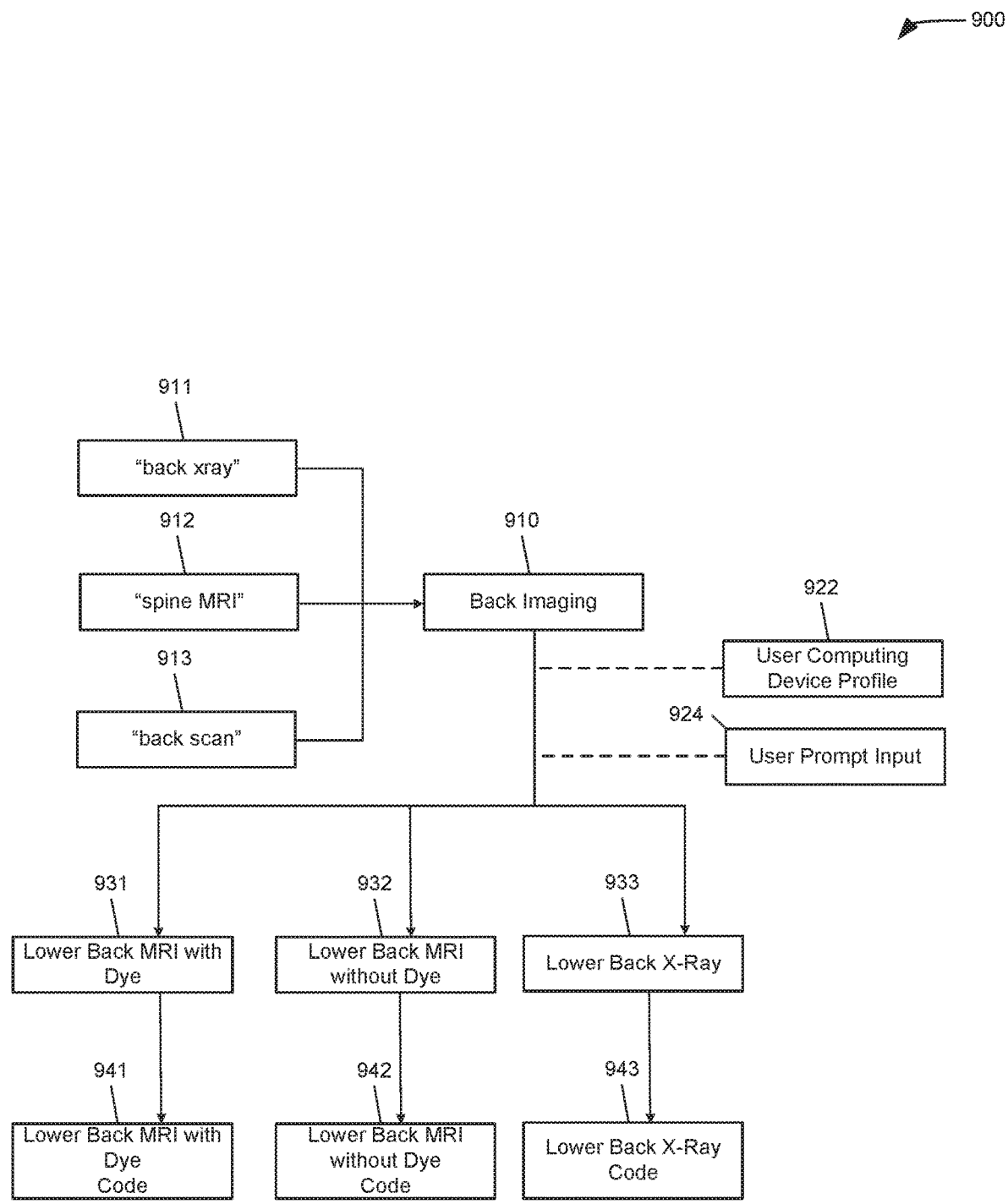

FIG. 9 illustrates applying the approach of the schema of FIG. 3 to define taxonomical classification 910 and define sub-classifications for services 931, 932, and 933 and associated service codes 941, 942, and 943. Again, while keywords 911, 912, and 913 are properties for the taxonomical classification of back imaging 910, there are also taxonomical sub-classifications 931, 932, 933, 941, 942, and 943 and it is not clear from the keywords which sub-classifications are appropriate. As in FIGS. 4, 6, 7, and 8, user computing device profiles 922 or user prompt inputs 924 may be used to distinguish to which service 931, 932, and 933 a user is directed by classification computer 230. In this example, classification computer 230 provides user prompts to elicit user prompt inputs and determine which service 931, 932, or 933 should have flows provided to it.

Figure 10:
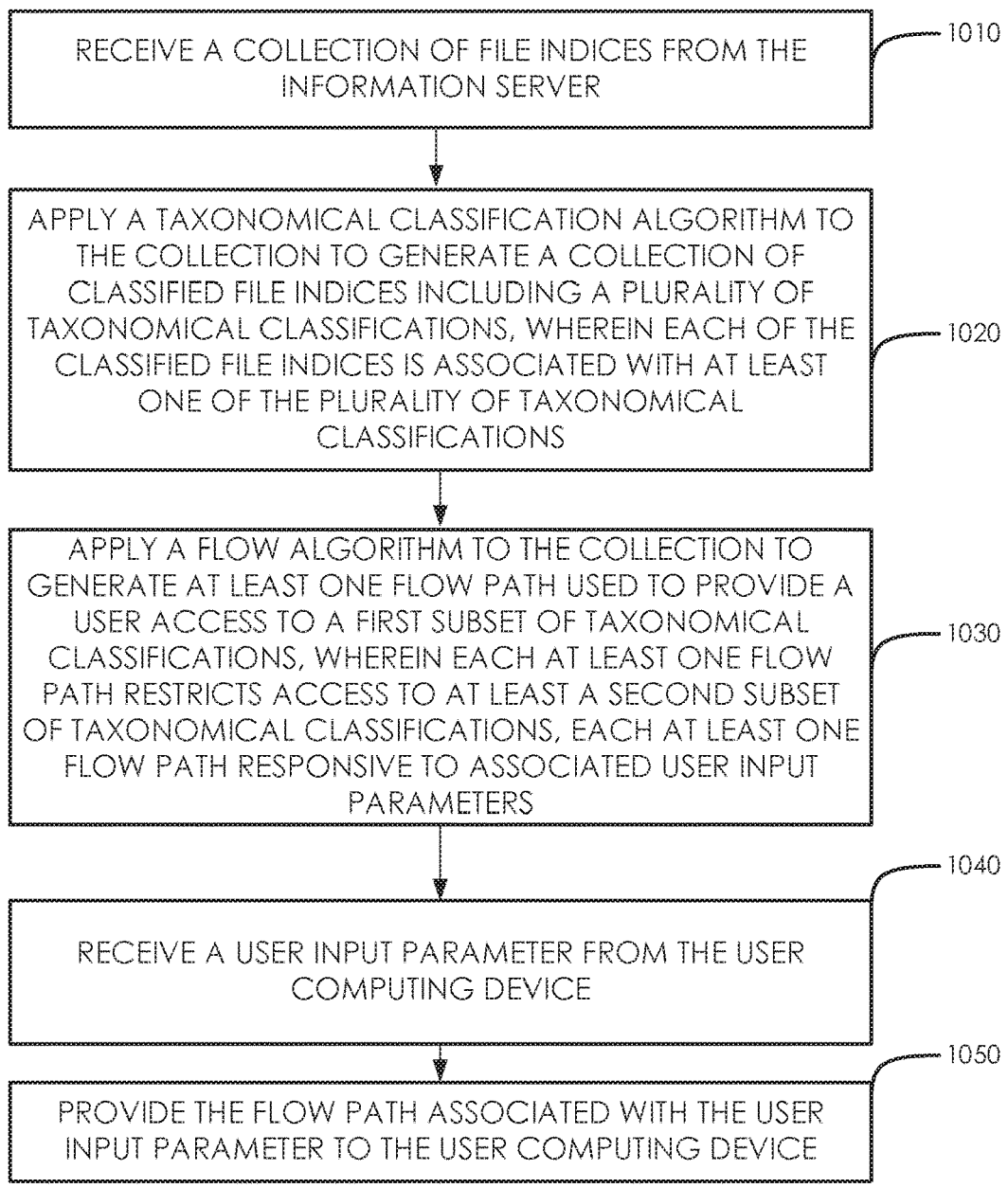
FIG. 10 is a flow diagram representing a method for providing adaptable taxonomies to facilitate user navigation of complex information systems performed by the classification computer shown in FIG. 2.

FIG. 10 is a flow diagram representing a method for providing adaptable taxonomies to facilitate user navigation of complex information systems performed by the classification computer 230 (shown in FIG. 2). Specifically, classification computer 230 receives 1010 a collection of file indices from the information server. Classification compute 230 also applies 1020 a taxonomical classification algorithm to the collection to generate a collection of classified file indices including a plurality of taxonomical classifications. Each of the classified file indices is associated with at least one of the plurality of taxonomical classifications. Classification computer 230 also applies 1030 a flow algorithm to the collection to generate at least one flow path used to provide a user access to a first subset of taxonomical classifications. Each at least one flow path restricts access to at least a second subset of taxonomical classifications. Each at least one flow path responsive to associated user input parameters. Classification computer 230 also receives 1040 a user input parameter from the user computing device. Classification computer 230 also provides 1050 the flow path associated with the user input parameter to the user computing device.

Figure 11:
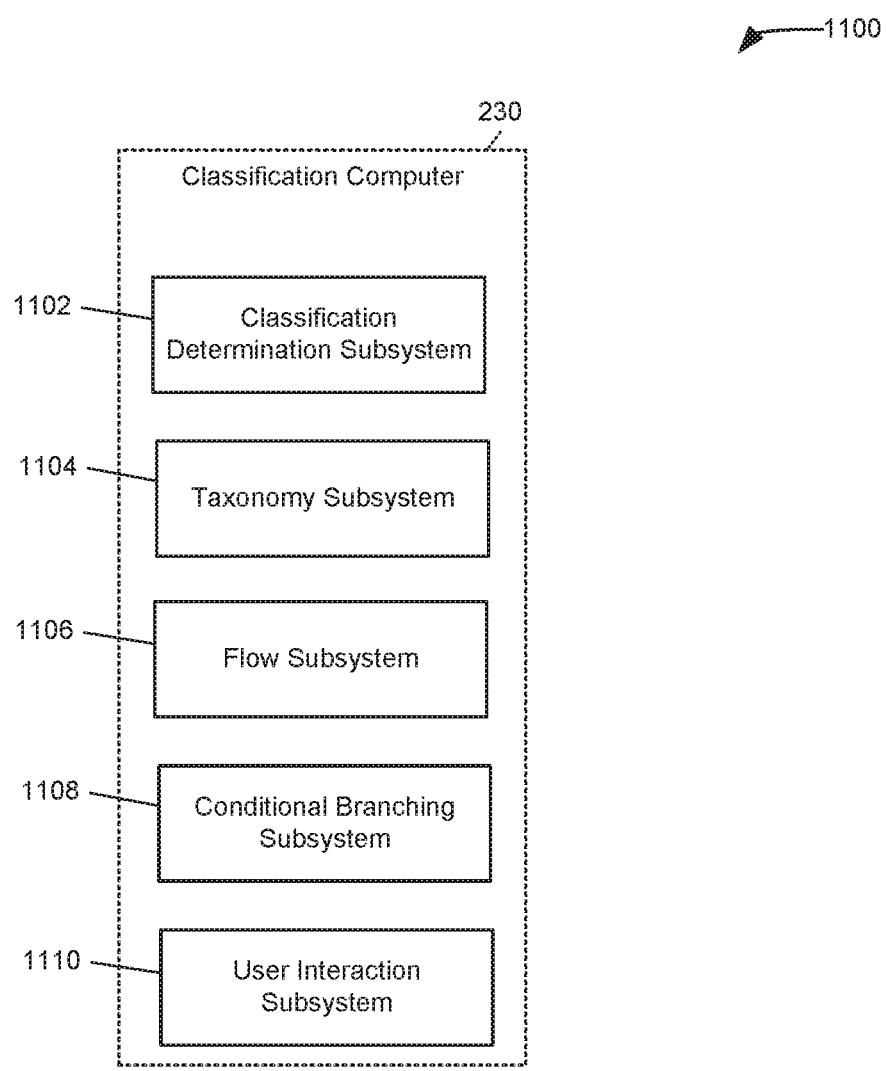
FIG. 11 is a diagram of elements of one or more example computing devices that may be used in the system shown in FIG. 2.

FIG. 11 is a diagram 1100 of elements of one or more example computing devices that may be used in the system shown in FIG. 2. Specifically, diagram 1100 depicts elements included in classification computer 230 (shown in FIG. 2) that are configured to perform the steps described herein. Classification determination subsystem 1102 is configured to define, control, and apply the taxonomical classification algorithm, and taxonomy subsystem 1104 is configured to define and maintain the adaptable taxonomies. Flow subsystem 1106 is configured to define and apply the flow algorithm used to create dynamic flows (including guided flows) to provide users with access to data. Conditional branching subsystem 1108 is configured to define the conditional branching criteria distinguishing taxonomical sub-classifications from one another based on, for example, distinct properties between them. User interaction subsystem 1110 is configured to generate and provide user interfaces for accessing the systems described herein including, for example, providing user computing devices with search query tools, navigation tools, and file viewing tools.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave). The term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A classification computing system for providing adaptable taxonomies and guided flow paths to facilitate user navigation of complex information systems, said classification computing system comprising:
   an information server comprising a server memory and a server processor;
   a user computing device comprising a device memory and a device processor; and
   a classification computer in communication with the information server and the user computing device, said classification computer comprising a memory and a processor, said processor configured to:
   receive a collection of file indices from the information server;
   analyze a plurality of files associated with the collection of file indices to generate a collection of classified file indices including a plurality of taxonomical classifications, wherein each of the classified file indices is associated with at least one of the plurality of taxonomical classifications;
   receive at least one user input parameter from the user computing device;
   analyze the at least one user input parameter to identify at least one keyword related to a first subset of the plurality of taxonomical classifications;
   apply a flow algorithm to passively obtain passive profile information from the user computing device and select at least one guided flow path based on the passive profile information and the at least one keyword, the at least one guided flow path configured to provide a user access to a first taxonomical classification in the first subset of the plurality of taxonomical classifications while restricting access to at least a second taxonomical classification in the first subset of the plurality of taxonomical classifications, the passive profile information describing one or more of the user or the user computing device;
   determine a plurality of conditional branches of the at least one guided flow path;
   generate a user prompt regarding the at least one guided flow path based on the plurality of conditional branches, the user prompt including one or more questions configured to directly elicit information from the user;
   receive a prompt response from the user computing device;
   apply the prompt response to the at least one guided flow path to identify, from the plurality of conditional branches, a responsive flow path included within the at least one guided flow path; and
   provide the responsive flow path associated with the prompt response, the passive profile information, and the at least one user parameter to the user computing device.

2. The classification computing system of claim 1, wherein said processor is further configured to:
   apply the prompt response to the at least one guided flow path to identify a responsive file included within the first subset of the plurality of taxonomical classifications and associated with the prompt response; and
   provide the responsive file to the user computing device.

3. The classification computing system of claim 1, wherein said processor is further configured to:
   provide the user prompt to the user computing device;
   wherein the prompt response is received from the user computing device in response to the user prompt.

4. The classification computing system of claim 1, wherein said processor is further configured to:
   receive input for a user screen associated with the user computing device, wherein the input for the user screen defines a set of information to not serve to the user computing device; and
   apply the input for the user screen to the at least one guided flow path to generate at least one screened flow path used to provide the user access to a screened portion of the first subset of the plurality of taxonomical classifications that does not include the set of information to not serve to the user computing device, wherein each at least one screened flow path restricts access to at least a second subset of the plurality of taxonomical classifications, each at least one screened flow path responsive to the prompt response, the passive profile information, and the at least one user input parameter.

5. The classification computing system of claim 1, wherein said passive profile information comprises a user profile including at least one of user demographics and user medical information.

6. The classification computing system of claim 1, wherein said at least one user input parameter comprises a search query including the at least one keyword, wherein said processor is further configured to analyze the plurality of files associated with the collection of file indices to determine at least one file containing the at least one keyword.

7. The classification computing system of claim 1, wherein said passive profile information includes a geographic location of the user computing device.

8. A classification computer for providing adaptable taxonomies and guided flow paths to facilitate user navigation of complex information systems, said classification computer in communication with an information server and a user computing device, said classification computer comprising a memory and a processor, said processor configured to:
receive a collection of file indices from the information server;
analyze a plurality of files associated with the collection of file indices to generate a collection of classified file indices including a plurality of taxonomical classifications, wherein each of the classified file indices is associated with at least one of the plurality of taxonomical classifications;
receive at least one user input parameter from the user computing device;
analyze the at least one user input parameter to identify at least one keyword related to a first subset of the plurality of taxonomical classifications;
apply a flow algorithm to passively obtain passive profile information from the user computing device, and select at least one guided flow path based on the passive profile information and the at least one keyword, the at least one guided flow path configured to provide a user access to a first taxonomical classification in the first subset of the plurality of taxonomical classifications while restricting access to at least a second taxonomical classification in the first subset of the plurality of taxonomical classifications, the passive profile information describing one or more of the user or the user computing device;
determine a plurality of conditional branches of the at least one guided flow path;
generate a user prompt regarding the at least one guided flow path based on the plurality of conditional branches, the user prompt including one or more questions configured to directly elicit information from the user;
receive a prompt response from the user computing device;
apply the prompt response to the at least one guided flow path to identify, from the plurality of conditional branches, a responsive flow path included within the at least one guided flow path; and
provide the responsive flow path associated with the prompt response, the passive profile information, and the at least one user parameter to the user computing device.

9. The classification computer of claim 8, wherein said processor is further configured to:
apply the prompt response to the at least one guided flow path to identify a responsive file included within the first subset of the plurality of taxonomical classifications and associated with the prompt response; and
provide the responsive file to the user computing device.

10. The classification computer of claim 8, wherein said processor is further configured to:
provide the user prompt to the user computing device;
wherein the prompt response is received from the user computing device in response to the user prompt.

11. The classification computer of claim 8, wherein said processor is further configured to:
receive input for a user screen associated with the user computing device, wherein the input for the user screen defines a set of information to not serve to the user computing device; and
apply the input for the user screen to the at least one guided flow path to generate at least one screened flow path used to provide the user access to a screened portion of the first subset of the plurality of taxonomical classifications that does not include the set of information to not serve to the user computing device, wherein each at least one screened flow path restricts access to at least a second subset of the plurality of taxonomical classifications, each at least one screened flow path responsive to the prompt response, the passive profile information and the at least one user input parameter.

12. The classification computer of claim 8, wherein said passive profile information comprises a user profile including at least one of user demographics and user medical information.

13. The classification computer of claim 8, wherein said at least one user input parameter comprises a search query including the at least one keyword, wherein said processor is further configured to analyze the plurality of files associated with the collection of file indices to determine at least one file containing the at least one keyword.

14. The classification computer of claim 8, wherein said passive profile information includes a geographic location of the user computing device.

15. A method for providing adaptable taxonomies and guided flow paths to facilitate user navigation of complex information systems performed by a classification computer, the classification computer in communication with an information server and a user computing device, the classification computer including a memory and a processor, said method comprising:
receiving a collection of file indices from the information server;
analyzing a plurality of files associated with the collection of file indices to generate a collection of classified file indices including a plurality of taxonomical classifications, wherein the classified file indices is associated with at least one of the plurality of taxonomical classifications;
receiving at least one user input parameter from the user computing device;

analyzing the at least one user input parameter to identify at least one keyword related to a first subset of the plurality of taxonomical classifications;

applying a flow algorithm to passively obtain passive profile information from the user computing device, and select at least one guided flow path based on the passive profile information and the at least one keyword, the at least one guided flow path configured to provide a user access to a first taxonomical classification in the first subset of taxonomical classifications while restricting access to at least a second taxonomical classification in the first subset of the plurality of taxonomical classifications, the passive profile information describing one or more of the user or the user computing device;

determine a plurality of conditional branches of the at least one guided flow path;

generating a user prompt regarding the at least one guided flow path based on the plurality of conditional branches, the user prompt including one or more questions configured to directly elicit information from the user;

receiving a prompt response from the user computing device;

applying the prompt response to the at least one guided flow path to identify, from the plurality of conditional branches, a responsive flow path included within the at least one guided flow path; and providing the responsive flow path associated with the prompt response, the passive profile information, and the at least one user parameter to the user computing device.

16. The method of claim 15, further comprising:

applying the prompt response to the at least one guided flow path to identify a responsive file included within the first subset of the plurality of taxonomical classifications and associated with the prompt response; and providing the responsive file to the user computing device.

17. The method of claim 15, further comprising:

providing the user prompt to the user computing device, the user prompt including one or more questions;

wherein the prompt response is received from the user computing device in response to the user prompt.

18. The method of claim 15, further comprising:

receiving input for a user screen associated with the user computing device, wherein the input for the user screen defines a set of information to not serve to the user computing device; and applying the input for the user screen to the at least one guided flow path to generate at least one screened flow path used to provide the user access to a screened portion of the first subset of the plurality of taxonomical classifications that does not include the set of information to not serve to the user computing device, wherein each at least one screened flow path restricts access to at least a second subset of the plurality of taxonomical classifications, each at least one screened flow path responsive to the prompt response, the passive profile information, and the at least one user input parameter.

19. The method of claim 15, wherein the at least one user input parameter received from the user computing device comprises a search query including the at least one keyword.

20. The method of claim 15, the passive profile information includes a geographic location of the user computing device.

* * * * *